Jan. 27, 1976 A. M. SHAMMARELLO Plant Pat. 3,827
AZALEA PLANT
Filed Sept. 27, 1974
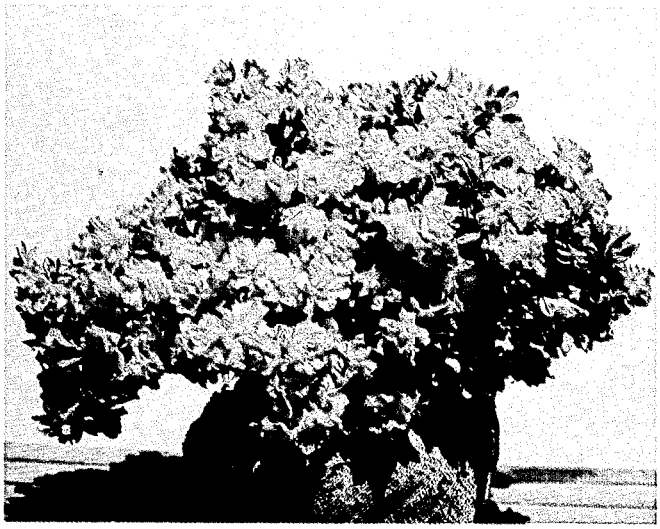

United States Patent

Plant Pat. 3,827
Patented Jan. 27, 1976

3,827
AZALEA PLANT

Anthony M. Shammarello, 4508 Monticello Blvd., South Euclid, Ohio 44143

Filed Sept. 27, 1974, Ser. No. 510,212
Int. Cl. A01h *5/00*
U.S. Cl. Plt.—56 1 Claim

The present invention relates to a new and distinct variety of azalea plant of the Kurume type, and is the result of a definite breeding program.

The principal object of this breeding program was to produce a new hardy, semi-double, pink flower azalea, such a plant is not known to me in Northern Ohio.

The foregoing objective has been obtained in my new variety by a hardy plant with semi-double pink flower and retention of foliage throughout the winter.

Seed parent: Azalea Helen Curtis, P.P. No. 2,837, granted Oct. 1, 1968 to Anthony M. Shammarello, the applicant herein.

Pollen parent: Azalea Hino-Red, P.P. No. 2,507, granted May 11, 1965 to Anthony M. Shammarello, the applicant herein.

My new variety has been found to retain its distinctive characteristics through successive asexual reproduction by means of cuttings in the vicinity of South Euclid, Ohio.

The hardiness of the plant and flower buds of my new variety is indicated by the fact that they were not adversely affected by a temperature of 12 degrees below zero the winter of 1973–1974 in the vicinity of South Euclid, Ohio.

The flowers of my new variety are about 2¼ inches wide, composed of three rows of florets slightly frilled.

The accompanying drawing, forming a part hereof, shows a typical plant of my new variety of azalea, the color of the latter being as nearly as it is reasonably possible to make the same in a color illustration of this character.

The following is a detailed description of my new variety of azalea plant, color reference being to the Nickerson Color Fan by the Munsell Color Company.

*Type:* Hardy—evergreen.
*Parentage:* Seedling.
*Seed parent:* Azalea Helen Curtis, P.P. No. 2,837.
*Pollen parent:* Azalea Hino-Red, P.P. No. 2,507.

PLANT

*Form of plant:* Bushy compact, close to ground, horizontal.
*Growth habit:* Medium, from a cutting attaining a height of about 12 to 15 inches and width of about 18 to 24 inches in five years.
*Blooming season:* About May 20th.

Color reference to Nickerson Color Fan.

*Young shoots:* Stem color 2.5 YR 5/9 brownish orange.
*Mature shoots:* Stem color 10 YR 3/1 brownish gray.
*Foliage:* Color of young leaves (obverse) 2.5 GY 5/5 moderate yellowgreen. Color of mature leaves (obverse) 5 GY 4/3 moderate green. Color of leaves (reverse) 2.5 GY 5/5 moderate yellow green.
*Arrangement of leaves:* In a spiral.
*Form of leaves:* Elliptical.
*Size of leaves:* 1¾ to 2 inches long. ¾ inch to 1 inch wide.
*Leaf texture:* Firm.
*Pubescence of leaves:* Short white hairs covering all of underside area.

FLOWER

*Type:* Semi-double, three rows of petals.
*Borne:* Usually three in a cluster.
*Quantity:* Abundant.
*Form:* Fifteen petals, 5 lobes, slightly frilled.
*Size:* Petal spread 2 to 2½ inches wide.
*Color:* Between 10 HP 6/12 deep pink and 10 HP 5/12 strong purplish red.
*Blotch:* None.
*Petal texture:* Firm, with substance.
*Fragrance:* None.
*Stamens:* Color 5 R 5/13 with vivid red, quantity 5 to 6, 2 or 3 stamens individually formed, 2 or 3 stamens attached to florets, 1 inch long.
*Pistil:* Color 5 R 4/12 strong red, 1¼ inches long.
*Flower bud hardiness:* Twelve degrees below zero.

I claim:

1. A new and distinct variety of azalea plant of the hardy evergreen type, substantially as herein shown and described, characterized particularly as to novelty by the radiant pink color of its semi-double hose-in-hose flowers, by the absence of fading of the flowers when exposed to the sun, by the long lastingness of color of flowers, by the plant forming a compact bush snug to the ground, by the hardiness of the plant and buds at low temperatures inheritant of the parent plants and retaining the good qualities of plant character of parent plants.

References Cited

The Azalea Handbook, The American Horticultural Society, 1952, pp. 13–15 cited.

ROBERT E. BAGWILL, Primary Examiner